United States Patent [19]
Wasserman et al.

[11] Patent Number: 6,090,059
[45] Date of Patent: Jul. 18, 2000

[54] ANKLET FOR FOOT ORTHOSIS

[75] Inventors: Constance V. Wasserman, Palm Harbor; Clarence E. Hess, Safety Harbor, both of Fla.

[73] Assignee: Restorative Care of America Incorporated, Clearwater, Fla.

[21] Appl. No.: 08/429,926

[22] Filed: Apr. 27, 1995

[51] Int. Cl.[7] .............................. A61F 5/00; A61F 13/00
[52] U.S. Cl. .............................. 602/27; 602/23; 602/60; 602/62
[58] Field of Search .................................. 602/23, 27, 60, 602/65, 28, 29; 129/DIG. 15; D24/190, 192; 24/712–715.7; 36/113, 114, 136, 123, 140

[56] References Cited

U.S. PATENT DOCUMENTS

| | | | |
|---|---|---|---|
| D. 375,164 | 10/1996 | Wasserman et al. | D24/192 |
| 4,401,113 | 8/1983 | Incorvaia | 602/65 |
| 5,052,128 | 10/1991 | Lonardo. | |
| 5,217,431 | 6/1993 | Toronto et al. | 602/65 X |
| 5,269,748 | 12/1993 | Lonardo | 602/27 |
| 5,368,551 | 11/1994 | Zuckerman | 602/23 |
| 5,372,576 | 12/1994 | Hicks | 602/27 |
| 5,403,265 | 4/1995 | Berguer et al. | 602/27 X |
| 5,429,588 | 7/1995 | Young et al. | 602/27 |
| 5,472,414 | 12/1995 | Detty | 602/27 |
| 5,486,157 | 1/1996 | DiBenedetto | 602/27 |

OTHER PUBLICATIONS

"Theraboot—Therapeutic Orthotic System" Author: Orthotic Rehabilitation Products, Inc. Place of publication: Florida, Jan. 1994.

*Primary Examiner*—Richard J. Apley
*Assistant Examiner*—Kim M. Lee
*Attorney, Agent, or Firm*—Zarley, Mckee, Thomte, Voorhees & Seas

[57] ABSTRACT

An anklet for a foot orthosis has a one-piece member having a sole portion, opposite side portions each terminating in a flap element, a heel portion and a fastening strap. The sole portion has a pocket to receive the foot portion of the orthosis. A soft liner is attached to the interior surface of the anklet. The fastening strap extends over the overlapped flap elements to reinforce the engaged fastening elements on the interior surface of the straps.

6 Claims, 1 Drawing Sheet

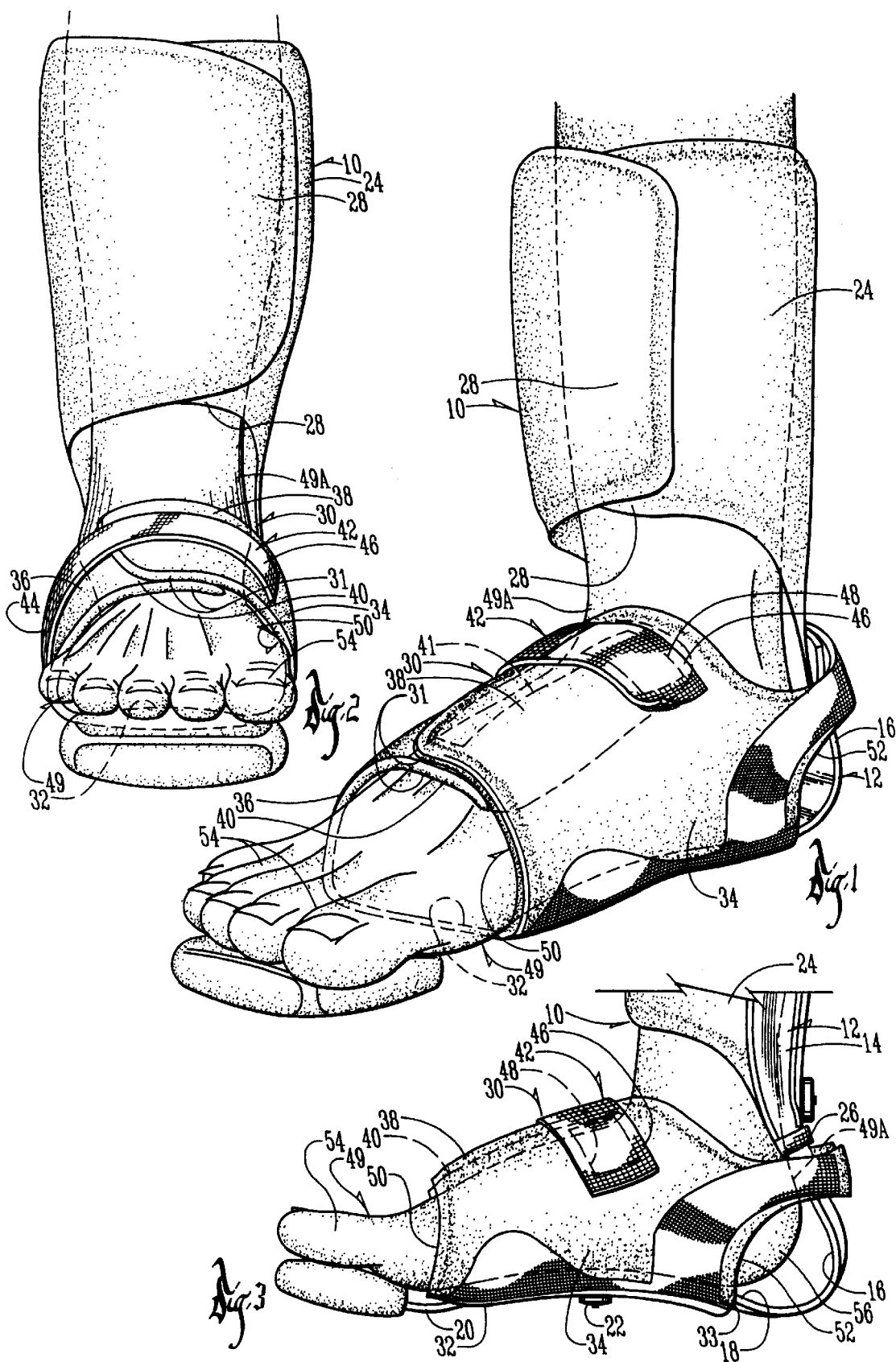

ANKLET FOR FOOT ORTHOSIS

BACKGROUND OF THE INVENTION

Foot orthosis comprising a plastic L-shaped member adapted for use in the lower leg and foot are commonly in use. They are normally secured to the foot by one or more pad and strap assemblies, one of which is an anklet which fits over the foot portion of the L-shaped member, and over the foot of the patient. Typical anklets are held in place by a plurality of straps that extend over the top of the patient's foot and which must be separately fastened or unfastened as the device is placed on, or removed from the patient. Care must be exercised in this process, and usually one of the plurality of straps must be fastened first for the best results.

This invention involves an improved anklet for a foot orthosis. A principal object of the invention is to provide an anklet for a foot orthosis that is easily attached to and detached from the foot of a patient.

A further object of this invention is to provide an anklet for a foot orthosis which will effectively hold the orthosis on the patient's foot.

These and other objects will be apparent to those skilled in the art.

SUMMARY OF THE INVENTION

The anklet of this invention is a one-piece member having a sole portion, opposite side portions each terminating in a flap element, a heel portion, and a fastening strap. The sole portion has a pocket to receive the foot portion of the orthosis. A soft liner is attached to the interior surface of the anklet. The fastening strap extends over the overlapped flap elements to reinforce the engaged fastening elements on the interior surface of the flaps.

BRIEF DESCRIPTION OF THE DRAWING

FIG. 1 is a perspective view of the anklet of this invention mounted on a foot orthosis;

FIG. 2 is a front elevational view of the anklet of this invention as seen from the left-hand side of FIG. 1; and FIG. 3 is a side elevational view of the anklet shown in FIG. 2 as seen from the right-hand side of FIG. 2.

DESCRIPTION OF THE PREFERRED EMBODIMENT

The numeral 10 designates a foot orthosis having an L-shaped plastic splint 12 including a leg portion 14, an enlarged heel portion 16, and a foot portion 18. A conventional toe plate 20 is secured to the bottom of the foot portion by means of bolt assembly 22.

A leg pad 24 is mounted around the leg portion 14 and has an elastic strap or band 26 at the lower portion thereof (FIG. 3) to extend around the splint at a point between the leg portion 14 and the heel portion 16. The leg pad 24 has an open seam in the front thereof comprised of a pair of overlapped flaps 28 which can have a conventional securing means thereon so that the flaps can be detachably secured to each other for purposes of attaching the leg portion of the splint to the lower leg of a patient.

The foregoing structure is conventional in foot orthosis and does not specifically comprise a part of this invention.

The anklet 30 having a soft liner 31 of this invention has a sole portion 32 (FIGS. 1 and 3), which has a pocket 33 (FIG. 3) in which the foot portion 18 is inserted. Pocket 33 is of conventional construction.

Anklet 30 has a pair of sidewalls 34 and 36 which extend upwardly from the sides of the sole portion 32 and terminate in flaps 38 and 40, respectively. A hook fastener 41 (dotted lines in FIG. 1) is secured to the inner surface of flap 38 and is adapted to attach itself upon the application of pressure to the flap 40 through the conventional features of hook and loop fasteners. A strap 42 has a lower end 44 which is secured to the lower part of sidewall 36. The opposite free end 46 of strap 42 has a hook fastener 48 (dotted lines of FIG. 1) secured thereto and is adapted to extend upwardly over sidewall 36 and onto flap 38 for attachment to the flap 38. It should be noted that the strap 38 is located high on the upper surface of the patient's foot 49 immediately adjacent the point where the foot joins the lower leg portion 49A (FIG. 3).

Anklet 10 has a conventional open toe end 50 and an open heel end 52.

The numeral 54 represents the toes of the patient and the numeral 56 represents the heel of a patient's foot.

In operation, the flaps 28 on leg pad 24 are released into an open condition as are the flaps 38 and 40 on anklet 30. The patient's foot is placed into the foot orthosis, and the flaps 28 are closed upon each other in the manner described so that the pad 24 embraces the lower leg of the patient.

The flap 38 is then placed over the flap 40 as best shown in FIGS. 1 and 2 so that the two flaps firmly engage the sidewalls 34 and 36 against the foot of the patient. The fastening strap 42 is then raised upwardly over the surface of sidewall 36 and thence over and across the flap 38. By applying pressure to the free end 46 of strap 42, the hook fastener 48 engages the material of the anklet and the strap is held firmly in place. It has been determined that having the strap extend upwardly over flap 18 from sidewall 36 results in a much better arrangement than having a strap extend from flap 38 to be detachably secured to sidewall 36.

It should be understood the line of demarcation between the flaps on the anklet and the sidewall is not critical nor is the precise line of demarcation from the sole portion 32 to the sidewalls of a critical nature. Thus, if the lower end of strap 42 was secured to the sole portion 32 rather than the sidewall 36, the result would be equivalent. Similarly, if the free end 46 of the strap 42 extended over flap 38 onto sidewall 34, an equivalent function would result.

It is therefore seen that the anklet of this invention can be easily attached to and removed from a patient's foot. While in an operative position, it will firmly and effectively remain in place. The objects of the invention are therefore seen to be fully achieved.

What is claimed is:

1. An anklet for a foot orthosis comprising,
    a sheet member having a sole portion having side edges that extend upwardly into opposite sidewalls which each have an upper edge that terminates in a flap element which are adapted to be pulled over the top of a patient's foot in overlapping condition with one flap element engaging the patient's upper foot, and the other flap extending over said one flap element,
    a fastening means between said flap elements to detachably secure them together; and
    a fastening strap fixed to one sidewall and extending upwardly over the top of said other flap element and being detachably secured thereto, said fastening strap being secured to the other flap element by means of a hook and loop fastener.

2. The anklet of claim 1 wherein said fastening means comprises a hook and loop fastener.

3. The anklet of claim 1 wherein said sheet member has an open toe portion.

4. The anklet of claim 1 wherein said sheet member has an open toe portion and an open heel portion.

5. The anklet of claim 1 wherein said sole portion has a pocket to receive the foot portion of a foot orthosis.

6. An anklet for a foot orthosis, comprising:

a sheet member having a sole portion with opposite side edges, first and second sidewalls extending upwardly from the side edges, and first and second flaps extending from the respective first and second sidewalls, the first flap being adapted to overlap the second flap to define an overlap area, with the overlap being in a first lateral direction;

fastening means on the overlap area of at least one of the flaps to releasably secure the flaps together;

a fastening strap securely connected to the second flap and being adapted to overlap the first flap for releasable securement to the first flap, with the overlap being in a second lateral direction opposite the first lateral direction.

\* \* \* \* \*